United States Patent [19]

Kaihara et al.

[11] Patent Number: 5,057,691
[45] Date of Patent: Oct. 15, 1991

[54] DILUTION MATERIAL, FILTER AND ACCESSORY FOR MEASURING INFRARED SPECTRA

[75] Inventors: Mikio Kaihara; Hiroaki Mametsuka, both of Tokyo; Naoki Gunji, Kanagawa; Hideo Iwata, Kanagawa; Yohichi Gohshi, Kanagawa, all of Japan

[73] Assignee: NKK Corporation, Tokyo, Japan

[21] Appl. No.: 460,463

[22] Filed: Jan. 3, 1990

[30] Foreign Application Priority Data

Jun. 28, 1989 [JP] Japan .................................. 1-163800

[51] Int. Cl.$^5$ .......................................... G01N 21/01
[52] U.S. Cl. ..................................... 250/339; 250/353
[58] Field of Search ........................ 436/166, 171, 179; 252/587; 350/1.1, 1.5, 1.6; 250/353, 339

[56] References Cited

U.S. PATENT DOCUMENTS

| 4,661,706 | 4/1987 | Messerschmidt et al. | 250/341 |
| 4,721,657 | 1/1988 | Takahashi et al. | 428/689 |
| 4,853,542 | 8/1989 | Milosevic et al. | 250/353 |

FOREIGN PATENT DOCUMENTS

| 63-261142 | 10/1988 | Japan | 250/339 |
| 01-98947 | 4/1989 | Japan . | |
| 01-98948 | 4/1989 | Japan . | |
| 01-169341 | 7/1989 | Japan | 250/339 |
| 02-28540 | 1/1990 | Japan . | |
| 2104528 | 3/1983 | United Kingdom | 252/587 |

OTHER PUBLICATIONS

Derwent World Patent Index citations for JP 02-028540, JP 01-098948 and JP 01-098947 (includes English language abstract) 2 Pages.
G. O. Brunner, H. Reifler and E. Kleber, "Wide-Angle Beam Condesnor for Recording IR Transmission Spectra of Strongly Scattering Samples in the 3000 cm$^{-1}$ Region," *Rev. Sci. Instrum.*, vol. 57, No. 2 (Feb. 1986), pp. 295-296, [1986 American Institute of Physics].
M. Kaihara et al., "New Dilution Materials for Sensitivity Enhancement in the FT-IR Spectroscopy of Pitches as Typical Highly Scattering Samples" *Applied Spectroscopy* vol. 43; No. 3; pp. 477-480; (Mar./Apr. 1989).
M. Kaihara et al. "New Dilution Materials for Sensitivity Enhancement in IR Spectroscopy of Highly Scattering Samples"; *Journal of the Spectroscopical Society of Japan*; vol. 38 No. 1; pp. 35-38; 1989.
M. Kaihara et al.; "New Characterization Technique for Pitches by FT-IR Spectroscopy" No. 137, pp. 88-92; Jan. 10, 1989.
M. Kaihara et al., "New Accessory for Strongly Scattering Samples in Fourier-Transform Infrared Spectroscopy"; *Review of Scientific Instruments*; vol. 60; No. 6; pp. 1015-1017; Jun. 1989.
E. H. Korte et al., "Infrared Diffuse Reflectance Accessory for Local Analysis on Bulky Samples"; *Applied Spectroscopy*; vol. 42; No. 1; pp. 38-43; 1988.
E. H. Korte; "Figures of Ment for a Diffuse Reflectance Accessory using on On-Axis Ellipsoidal Collecting Mirror"; *Applied Spectroscopy*; vol. 42; No. 3; pp. 423-433; 1988.

*Primary Examiner*—Constantine Hannaher
*Attorney, Agent, or Firm*—Sughrue, Mion, Zinn, Macpeak & Seas

[57] ABSTRACT

A dilution material for measuring infrared spectra comprising two or more kinds of the inorganic materials capable of transmitting infrared rays, of which the surface reflection loss is less than one third, and at least one of which the refractive index is different from another one by more than 0.1, and other means capable of improving infrared spectra of highly scattering samples such as coal powder and pitch powder.

9 Claims, 7 Drawing Sheets

DILUTION MATERIAL, FILTER AND ACCESSORY FOR MEASURING INFRARED SPECTRA

BACKGROUND OF THE INVENTION

1. Field of the Invention

This invention relates to a dilution material, a filter and an accessory for measuring infrared spectra.

2. Description of the Prior Art

When the infrared spectra of a material are measured, the sample is, in general, diluted prior to the measurement. Infrared spectroscopy is divided into the solution method, the paste method, the pellet method and the like according to the dilution method. Among them, the pellet method is widely utilized because of its superiorities with a small amount of a sample, sharp absorption spectra, no absorption spectra of a solvent, simple operation and the like. In the pellet method, the dilution materials for samples are potassium bromide, potassium chloride, sodium chloride, potassium iodide and the like, because they have no absorption peak in the infrared region and have plastic properties under pressure.

In the case of measuring the infrared spectra of highly scattering heterogeneous samples such as coals and pitches, infrared rays are scattered by the sample, and while a considerable quantity of infrared rays passes through the sample without contacting. Therefore, the background is great, and the absorption peaks are small. Heretofore, the background was eliminated by subtracting the baseline assumed to be straight lines or curves from the spectra (Y. Osawa, et al., J. Fuel Soc. Japan, 48,703, 1969, P. R. Solomon, et al., Fuel, 61,663, 1982). Such a correction method is inaccurate, because the supposed baseline composed of straight lines or curves is not the true baseline and is made by the perception of a human.

SUMMARY OF THE INVENTION

An object of the invention is to provide means to decrease the background of a highly scattering sample.

Another object of the invention is to provide means to obtain sharp absorption spectra even in the case of a highly scattering sample.

In order to achieve the above objects, the inventors have investigated, and found that, when two or more kinds of inorganic materials capable of transmitting infrared rays, having a good surface reflection and at least one of which the refractive index is different from another one by more than 0.1 are used as the dilution material for preparing the pelletized sample, the background of highly scattering samples is remarkably decreased and the peaks of absorption spectra are made remarkably sharp. Moreover, when a prism or a reflecting mirror is set so as to gather the infrared rays scattered or reflected from the pelletized sample, the background and the peaks of absorption spectra of highly scattering samples are further improved. When the prism and the reflecting mirror are made of two or more kinds of the inorganic materials as mentioned above, the background and the peaks of absorption spectra of highly scattering samples are further improved. When an infrared rays-scattering filter made of two or more kinds of the inorganic materials mentioned above is set behind the pelletized sample, the background and the peaks are further improved.

The present invention has been completed based upon the above findings, and thus provides a dilution material for measuring infrared spectra comprising two or more kinds of inorganic materials capable of transmitting infrared rays, of which the surface reflection loss is less than one third, and at least one of which the refractive index is different from another one by more than 0.1, an accessory for measuring infrared spectra comprising a prism or a reflecting mirror which is disposed surrounding a pelletized sample and an infrared rays-scattering filter being in contact with or close to the back of the pelletized sample, which gathers the scattered infrared rays and the reflected infrared rays emitted from the pelletized sample, and a method of measuring infrared spectra which comprises disposing an infrared rays-scattering filter made of two or more kinds of the inorganic materials mentioned above behind a pelletized sample which is uniformly dispersed in a dilution material comprising two or more kinds of the inorganic materials mentioned above, and measuring the infrared spectra.

DETAILED DESCRIPTION OF THE INVENTION

Figure 1:
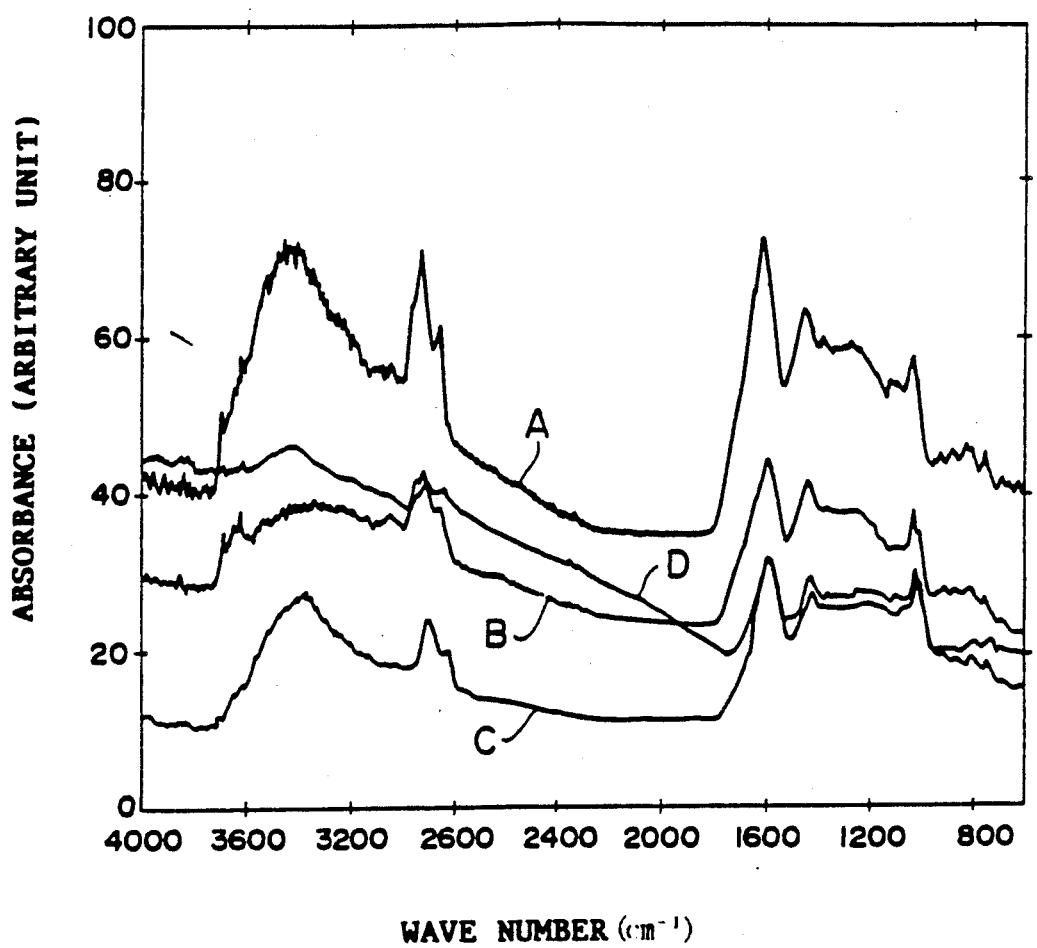
FIGS. 1 and 2 are graphs showing infrared spectra of a coal sample measured according to the invention in comparison with a conventional manner, respectively.

The dilution material for measuring infrared spectra is formed of two or more kinds of inorganic materials of which the refractive indexes are different from each other, and at least one of which the refractive index is different from another one by more than 0.1. Every inorganic material forming the dilution material has a small surface reflection loss and it must transmit infrared rays. Less surface reflection loss is more preferred, and it is less than one third, preferably less than one fifth. In general, the inorganic material preferably has a transmissibility through the wave length range from 600 $cm^{-1}$ to 4000 $cm^{-1}$. Higher transmissibility is more preferred, and for example, the transmittance at the thickness of 5 mm is preferably more than 60 %.

Examples of the inorganic material suitable for the dilution material are NaCl (refractive index; 1.519), KBr (refractive index; 1.526), KRS-5 (refractive index; 2.371), KRS-6 (refractive index; 2.177), AgCl (refractive index; 1.980, CsI (refractive index; 1.738), CsBr (refractive index; 1.662), Si (refractive index; 3.422), solid solutions thereof and the like. When KBr is employed as one of the inorganic materials, suitable inorganic materials combined with KBr are KRS-5, KRS-6, AgCl, Si, CsI, CsBr and the like. NaCl is not suitable, because the difference of the refractive index is too small. Preferable partners are CsI, CsBr and solid solutions thereof. The surface reflection losses of KRS-5 and KRS 6 are 24 to 28 % which is relatively great. The surface reflection loss of AgCl is 20 % which is also relatively great, and, moreover, the transmittance at the both ends of the measuring wave length region is not so high. When KCl, NaCl, KI or the like is employed as one of the inorganic materials, another inorganic material combined with any of them may be selected similarly. In the case of using the dilution material for pelletizing a sample, at least one of the inorganic materials must exhibit plasticity under pressure, such as an alkali halide including KBr, CsI, NaCl and the like. When two kinds of the inorganic materials are employed, a suitable mixing ratio is in the range of 95 : 5 to 5 : 95 by weight. In the case of the combination of CsI with KBr, a suitable mixing ratio by weight of CsI : KBr is also in the range of 95 : 5 to 5 : 95, and the range of 30 : 70 to 80 : 20 is preferred.

Various dilution materials were prepared by mixing CsI powder and KBr powder in various mixing ratios. The particle size of both of the CsI powder and KBr powder was under 125 μm. A coal powder was employed as a sample, and mixed sufficiently with each of the above dilution materials. Each mixture was pressed into a disc under vacuum, and the peak height around 1600 cm$^{-1}$ was measured. The results are summarized in Table 1.

TABLE 1

| CsI (wt. %) | KBr (wt. %) | Peak Height (mm) |
|---|---|---|
| 0 | 100 | 22 |
| 5 | 95 | 23 |
| 20 | 80 | 29 |
| 40 | 60 | 32 |
| 60 | 40 | 42 |
| 80 | 20 | 31 |
| 95 | 5 | 24 |
| 100 | 0 | 22 |

The dilution material may be prepared by mixing the inorganic materials. In such a case, a suitable particle size of each inorganic material is 1 to 100 μm, and the range of 3 to 20 μm is preferred.

On the other hand, once two or more kinds of the inorganic materials are dissolved and then deposited from the solution, a dilution material having excellent qualities can easily be obtained. For applying this method, each inorganic material is necessarily water-soluble, and therefore, AgCl, Si and the like are not suitable for this method. The solubility may be not so high. The solvent may be water alone or a mixed solvent of water and a hydrophilic solvent such as alcohol or acetone. Preferable solvents do not contain other inorganic materials, and are purified by ion-exchange, distillation, reverse osmosis or the like. The deposition of the inorganic materials from the aqueous solution may be carried out by any means other than the addition of an unevaporable material, and for example, concentration, cooling or the addition of a hydrophilic organic solvent can be utilized. The particle size of the deposited materials is preferably less than 100 μm, and less than 20 μm such as 2 to 20 μm, is particularly preferred. For that purpose, the speed of concentration, cooling and adding the hydrophilic organic solvent is made high, and the solution is stirred. The deposition rate is adjusted so that the deposited mixture has a prescribed mixing ratio. In view of obtaining a mixture of the inorganic materials having a prescribed mixing ratio easily, the aqueous solution is preferably evaporated to dryness without separating the deposited materials. When the deposited materials are separated from the mother liquid, the separation means may be conventional, such as centrifuging or filtration. The drying means may also be conventional, such as heating or pressure reducing. The dilution material prepared by the above deposition method is an uniform mixture of fine particles of the inorganic materials.

The dilution material can be used similar to conventional dilution materials, and after mixing it with a sample uniformly, the mixture is pressed into a prescribed shape under vacuum. The mixing ratio to a sample may be similar to a conventional one. Each inorganic material may be mixed in a prescribed ratio before the use or mixed together with a sample to be measured.

When an infrared rays-scattering filter made of two or more kinds of the inorganic materials capable of transmitting infrared rays, of which the surface reflection loss is less than one third, and at least one of which the refractive index is different from another one by more than 0.1 is disposed behind a sample pelletized by using the aforementioned dilution material, the background and the peaks of infrared absorption spectra are further improved.

The material forming the infrared rays-scattering filter is selected from the aforementioned dilution material. The material forming the filter may be the same as or different from the dilution material of the pelletized sample. A suitable thickness of the filter is in the range of 0.5 to 5 mm. The shape of the filter may be a disc having the same or a different diameter as the pelletized sample, or the like. A preferred filter is dish-shaped of which the recess portion is just for fitting the pelletized sample. The infrared rays scattering filter may be prepared by mixing the inorganic materials uniformly and then pressing into a prescribed shape under vacuum In a system where respective inorganic materials are separately crystallized by cooling, the inorganic materials are melted and poured into a mold. In order to produce fine crystals, the mold is preferably rapidly cooled.

The infrared rays-scattering filter is set behind the pelletized sample, i.e. opposite to the incident side of infrared rays. The filter is preferably in contact with or close to the pelletized sample, and preferably covers all faces of the sample except the incident portion of the infrared rays. In this regard, the aforementioned dish-shaped filter is particularly preferred.

A disc-shaped infrared rays-scattering filter was prepared. The filter was composed of 60 wt. % of CsI under (125 μm) and 40 wt. % of KBr (under 125 μm) and had a size of 10 mm in diameter and 1 mm in thickness. The filter was set behind each of the pelletized samples prepared in the measurement of Table 1 so as to contact the sample, and the peak height around 1600 cm$^{-1}$ was measured. The results are summarized in Table 2.

TABLE 2

| CsI (wt. %) | KBr (wt. %) | Peak Height (mm) |
|---|---|---|
| 0 | 100 | 45 |
| 5 | 95 | 46 |
| 20 | 80 | 64 |
| 40 | 60 | 65 |
| 60 | 40 | 71.5 |
| 80 | 20 | 61 |
| 95 | 5 | 46 |

When the infrared spectra of highly scattering sample are measured by the pellet method, it is effective to provide an accessory, which is a prism or a reflecting mirror, so as to surround the pelletized sample and an infrared rays-scattering filter being in contact with or close to the back of the pelletized sample.

Figure 10:
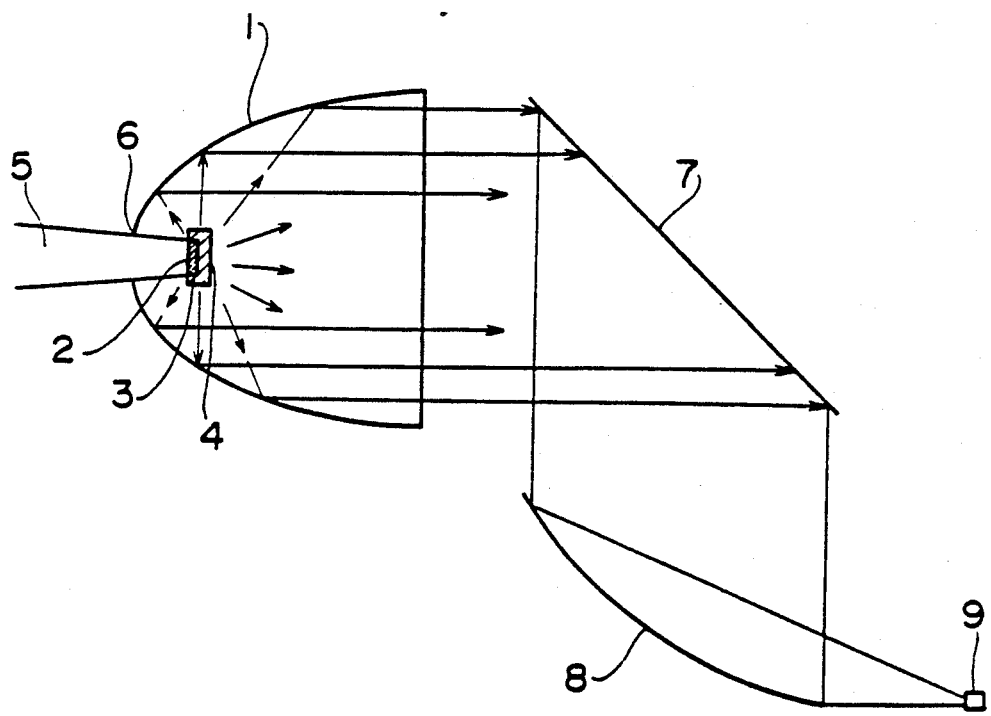
FIGS. 10 through 14 are schematic sectional views showing the states of using various accessories.

An embodiment of using the accessory is shown in FIG. 10. As illustrated in the drawing, a pelletized sample 3 is positioned at the focal point 2 of a reflecting mirror 1. The sample 3 is fitted in the central recess of the dish shaped filter 4. Infrared rays 5 enter the reflecting mirror 1 at the incident portion 6, and irradiate the sample 3. Then, the infrared rays 5 pass through the sample or are reflected or scattered by the sample. The transmitted infrared rays are scattered by the filter 4. The infrared rays scattered forward are also condensed as well as those scattered backward. These rays emitted from the sample are gathered by the reflecting mirror 1, passed through a plane mirror 7 and a concave mirror 8, and focused on a detector 9.

Figure 11:
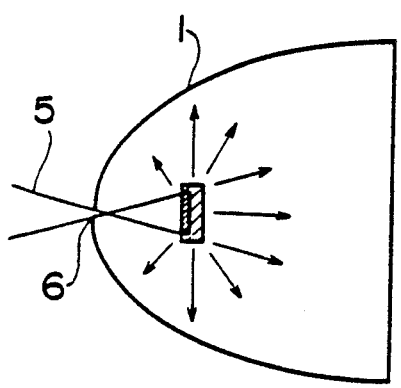
Figure 12:
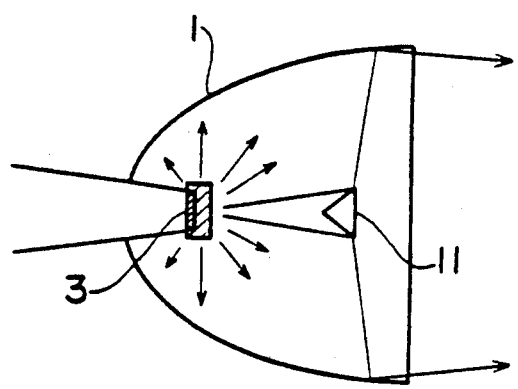
Figure 14:
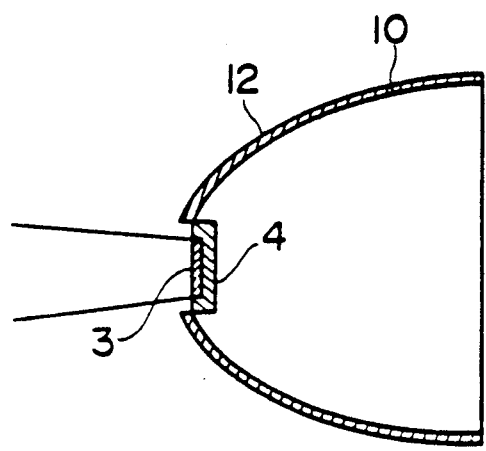

As mentioned above, an ellipsoid mirror, a paraboloid mirror or the like is used for the reflecting mirror. The diameter and the focal distance are determined according to respective infrared spectrophotometers. Generally, the pelletized sample is, as shown in FIG. 10, placed around the focal point. However, in view of taking a sample in and out easily, the sample 3 may be fitted into the reflecting mirror or a prism 10, as shown in FIG. 14. The reflecting mirror is necessarily to be provided with an incident portion for infrared rays to irradiate a sample and a mechanism for taking the sample in and out and supporting the sample at a prescribed position. In order to make the recovery of the scattered rays high, the area of the incident portion is preferably smaller. For that purpose, as shown in FIG. 11, incident infrared rays may be focused around the reflecting mirror face. In addition, as shown in FIG. 12, a reflecting plate 11 may be placed in the way of the rays passed through the sample 3 in the reflecting mirror 1, and the passed rays are reflected. The shape of the reflecting plate may be a plane, cone, sphere or the like.

Instead of the reflecting mirror, a prism 10 may be used as shown in FIG. 14. The prism is made in the form of an ellipsoid, paraboloid or the like. The prism is characterized by utilizing total reflection, and it is superior to the reflecting mirror in a high reflectance. Preferred materials for forming the prism have a high refractive index, such as KRS-5, KRS 6, KBr, NaCl, AgCl, CsI, CsBr and Si. As shown in FIG. 14, when the outer surface of the prism 10 is covered by an aluminum membrane 12 or the like, the recovery of the scattered rays is further improved. The use of the prism may be similar to the case of the reflecting mirror.

Figure 13:
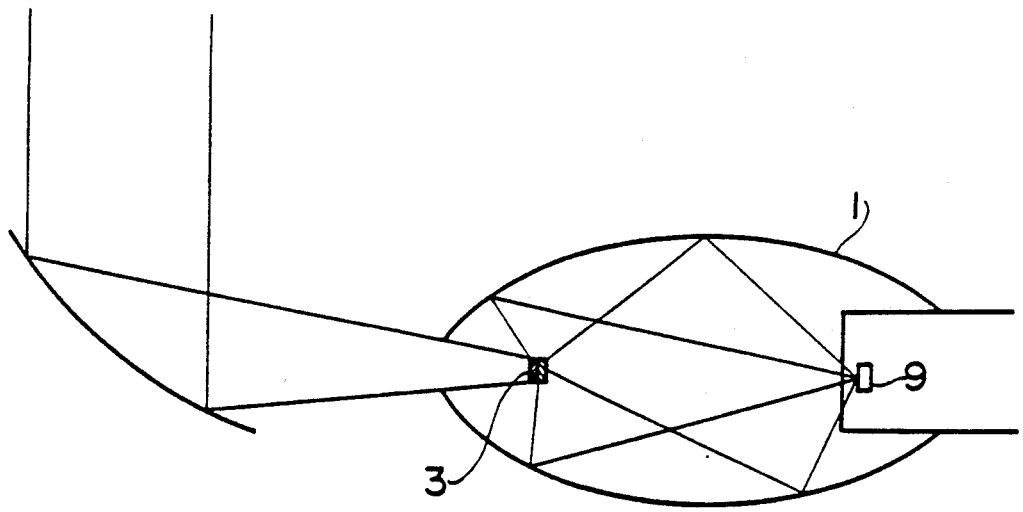

The rays gathered by the reflecting mirror or prism are focused on the detecting face of a detector, and concave mirrors, lenses and the like may be added for focusing Moreover, when it is necessary to move the optical path, plane mirrors and the like may also be added. As shown in FIG. 13, the reflecting mirror or the mirror is made in an elliptical sphere form, and the sample is placed at one of the focal points thereof and the detector is placed at the other focal point thereof. In that case, the reflecting mirror may be combined with the prism.

The effect of above accessories is increased by combining them with the aforementioned filter. In this regard, the size of the sample to be measured is preferably smaller. A suitable size of the sample correlates to the accessory employed, and in the case of an ellipsoid mirror, it is preferably less than one fifth of the minor axis.

In the case of a highly scattering heterogeneous sample, since the infrared rays irradiated to the sample are scattered, the incident quantity of the infrared rays containing the informations of the sample on the detector decreases. A considerable quantity of the infrared rays passes through the sample without contacting, the sample and elevates the background of the infrared spectra. When the dilution material of the invention is used, the inorganic materials having a different refractive index are aggregated at random in the sample portion. Therefore, the infrared rays deflect at the boundary portions between the inorganic materials, and multiple reflection occurs. As a result, scattering of the infrared rays is repeated, and the same ray meets the sample in many times. Thus, the information quantity of the sample contained in the ray increases, and the measuring sensitivity is elevated. When the particle size of the inorganic materials is made the same as about the wave length of infrared rays which is less than 20 $\mu$m, the scattering effect is further improved. Thus, the rays passing through the sample without contacting the sample become few, and, therefore, the background decreases. By using the dilution material of the invention, the absorption peaks are made sharp and high, and the background is remarkably decreased. As a result, new absorption peaks can be found, and the analytical accuracy of infrared spectra of highly scattering samples is improved. When an infrared rays-scattering filter is set behind the pelletized sample, the rays emitted form the sample are scattered by the filter, and a part of them returns to the sample. Thus, the absorption peaks are made more sharp, and the background is made lower. The accessory raises the recovery of scattered rays, and improves the signal to background (S/B) ratio and the signal to noise (S/N) ratio.

EXAMPLES

Example 1

60 wt. % of CsI fine powder (under 125 $\mu$m) was uniformly mixed with 40 wt. % of KBr fine powder (under 125 $\mu$m) to obtain the dilution material.

A coal powder sample was uniformly mixed with the dilution material, and pressed under vacuum into a disc 10 mm in diameter.

On the other hand, the same dilution material was pressed under vacuum into a disc 10 mm in diameter and 1 mm in thickness to obtain an infrared rays-scattering filter.

For comparison, the same coal powder sample was uniformly mixed with the conventional dilution material of KBr powder, and pressed under vacuum into a disc having the same shape and size as the above pelletized sample.

Infrared spectra of each pelletized sample were measured, and are shown in FIG. 1. In the figure, A indicates the spectra of the sample pelletized by using the dilution material of the invention behind which the above filter was set so as to be in contact with each other. B indicates the spectra of the above sample measured without using the filter. C indicates the spectra of the sample pelletized by using the conventional dilution material of KBr powder behind which the above filter was set so as to be in contact with each other. D indicates the spectra of the above conventional sample measured without using the filter. As shown in the figure, the peaks and the background of the infrared spectra were greatly improved by using the dilution material of the invention, and by incorporating the infrared rays scattering filter, they were further improved.

Example 2

60 wt. % of CsI fine powder (under 20 μm) was uniformly mixed with 40 wt. % of KBr fine powder (under 20 μm) to obtain the dilution material.

1.0 wt. % of a coal powder sample (under 149 μm) was uniformly mixed with 99 wt. % of the above dilution material, and pressed under vacuum into a disc 10 mm in diameter.

For comparison, the same coal powder sample was uniformly mixed with KBr powder (under 149 μm), and a conventional pelletized sample having the same shape and size was prepared similarly.

Figure 2:
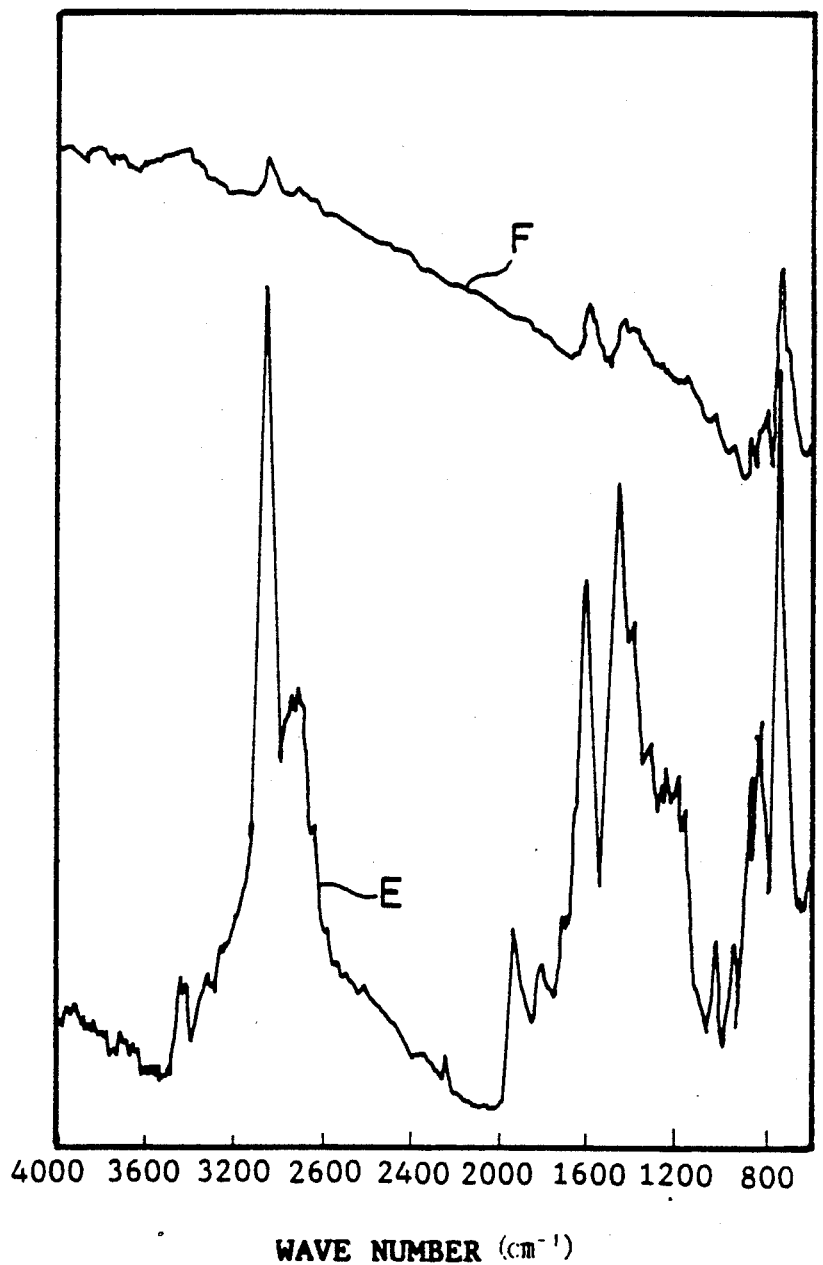

Infrared spectra of both pelletized samples were measured, and are shown in FIG. 2. In the figure, E indicates the spectra of the sample pelletized by using the dilution material of the invention, and F indicates the spectra of the conventional pelletized sample. As shown in the figure, by making the particle size of the dilution material less then 20 μm, the infrared spectra are more sharp, and the background is further decreased compared with the spectra of Example 1.

Example 3

CsI fine powder (under 20 μm) was uniformly mixed with KBr fine powder (under 20 μm) in various mixing ratios to obtain 4 kinds of the dilution materials.

Using the above dilution materials, pelletized samples of the same coal powder as Example 2 were prepared in the same manner as Example 2.

Figure 3:
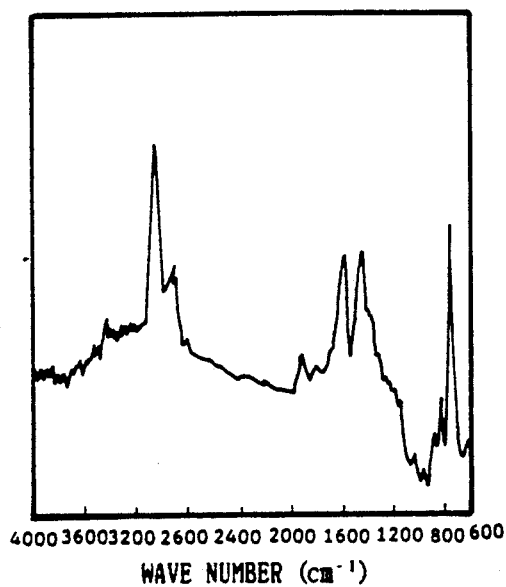
FIGS. 3 through 6 are graphs showing infrared spectra of a coal sample diluted with a mixture of CsI and KBr of which the mixing ratio is varied.
Figure 4:
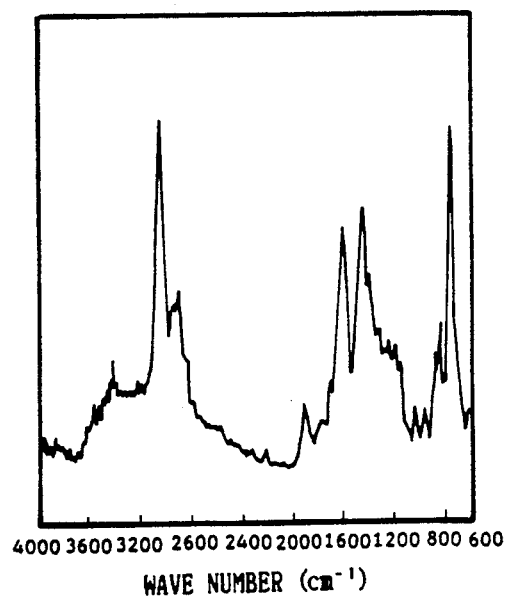
Figure 5:
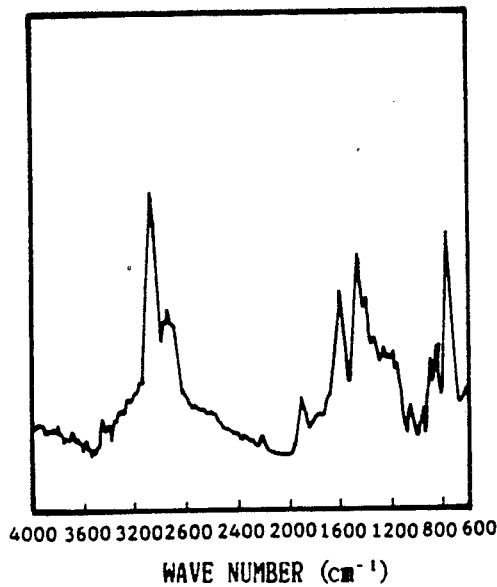
Figure 6:
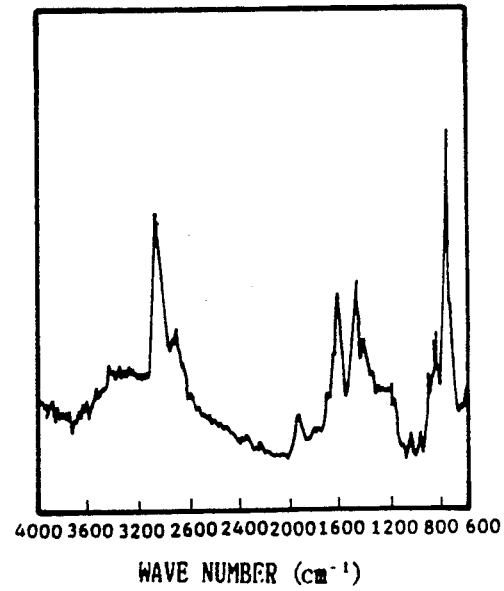

Infrared spectra of each pelletized sample were measured, and are shown in FIGS. 3 through 6. In the case of FIG. 3, the dilution material was composed of 20 wt. % of CsI and 80 wt. % of KBr, in the case of FIG. 4, the dilution material was composed of 40 wt. % of CsI and 60 wt. of KBr, in the case of FIG. 5, the dilution material was composed of 60 wt. % of CsI and 40 wt. % of KBr, and in the case of FIG. 6, the dilution material was composed of 80 wt. % of CsI and 20 wt. % of KBr.

Example 4

KBr and CsI were placed in a beaker in the ratio of 2 : 8, 4 : 6 or 6 : 4 by weight. Pure water purified by ion-exchange resins was gradually added to each beaker with stirring, until the whole amount of KBr and CsI were dissolved. Each solution was concentrated to dryness under reduced pressure, and the dried matter was further dried in a dryer at 107° C. overnight. The dried matter having a mixing ratio (KBr : CsI) of 4 : 6 was ground, and mixed uniformly with a pitch powder sample. The mixture was pressed under vacuum into a disc 10 mm in diameter.

KBr fine powder (under 125 μm) was uniformly mixed with CsI fine powder (under 125 μm) in a mixing ratio (KBr : CsI) of 4 : 6 by weight. The powder mixture was mixed uniformly with the same pitch powder sample, and the mixture was pressed under vacuum into a disc 10 mm in diameter.

For comparison, KBr and CsI were mixed in the ratio (KBr : CsI) of 4 : 6, and the mixture was melted and then solidified by cooling naturally. The solid matter was ground, and mixed uniformly with the same pitch powder sample. The mixture was pressed under vacuum into a disc 10 mm in diameter.

Also, for comparison, KBr was ground, and mixed uniformly with the same pitch powder sample. The mixture was pressed under vacuum into a disc 10 mm in diameter.

Figure 7:
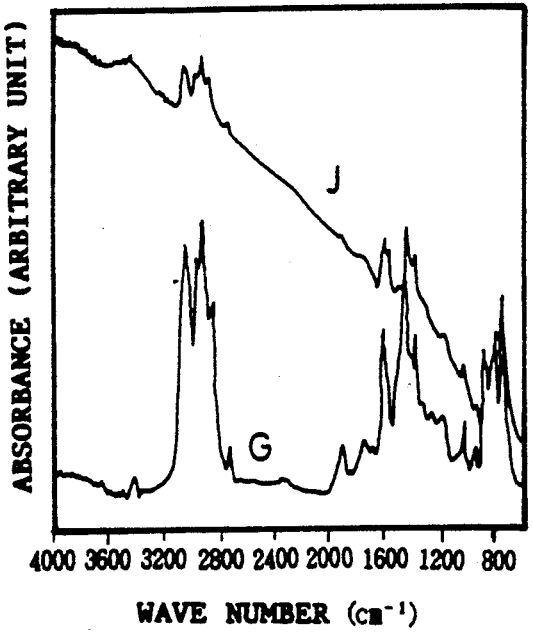
FIGS. 7 through 9 are graphs showing infrared spectra of a pitch sample diluted with a mixture of CsI and KBr prepared by various methods.
Figure 8:
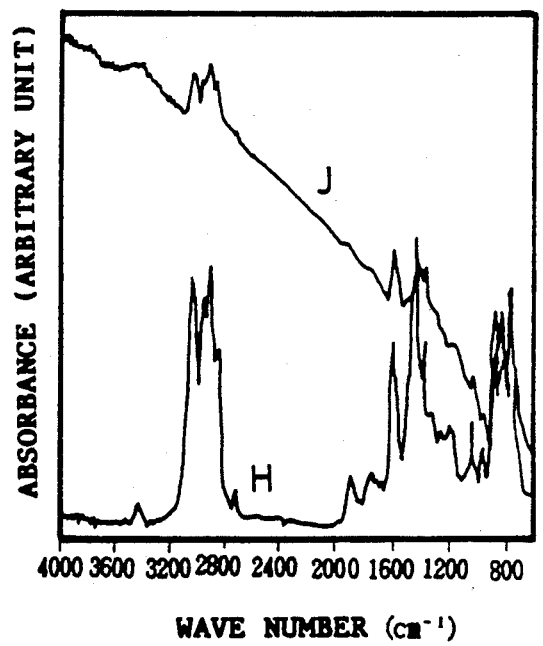
Figure 9:
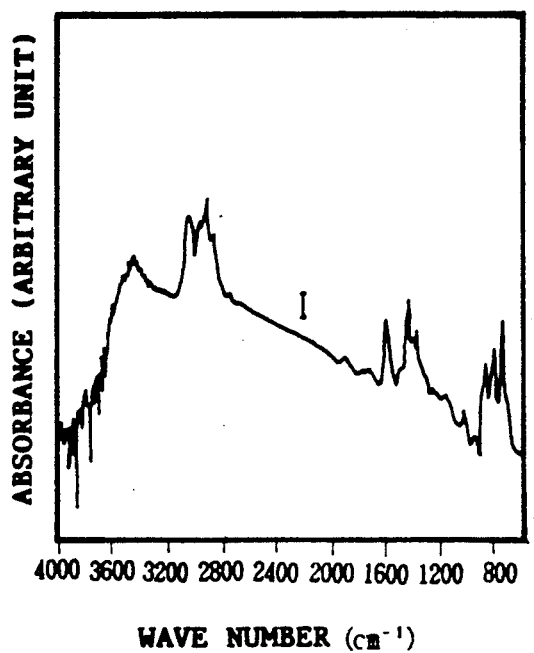

Infrared spectra of the above pelletized samples were measured and are shown in FIGS. 7 through 9. The spectra G in FIG. 7 was measured using the dilution material obtained through the one dissolution in water and then concentrated to dryness. The spectra H in FIG. 8 was measured using the dilution material obtained by the mere mixing of two powders. The spectra I in FIG. 9 were measured using the dilution material obtained through once melted. The spectra J in FIGS. 7 and 8 were measured using a conventional dilution material of KBr. As shown in the figures, when two kinds of the inorganic materials coexist in different phases, the peaks of infrared spectra are sharp, and the background is low. When the dilution material forms a single phase, the peaks are degraded, and the background increases, as shown in the spectra I and J.

Example 5

Figure 16:
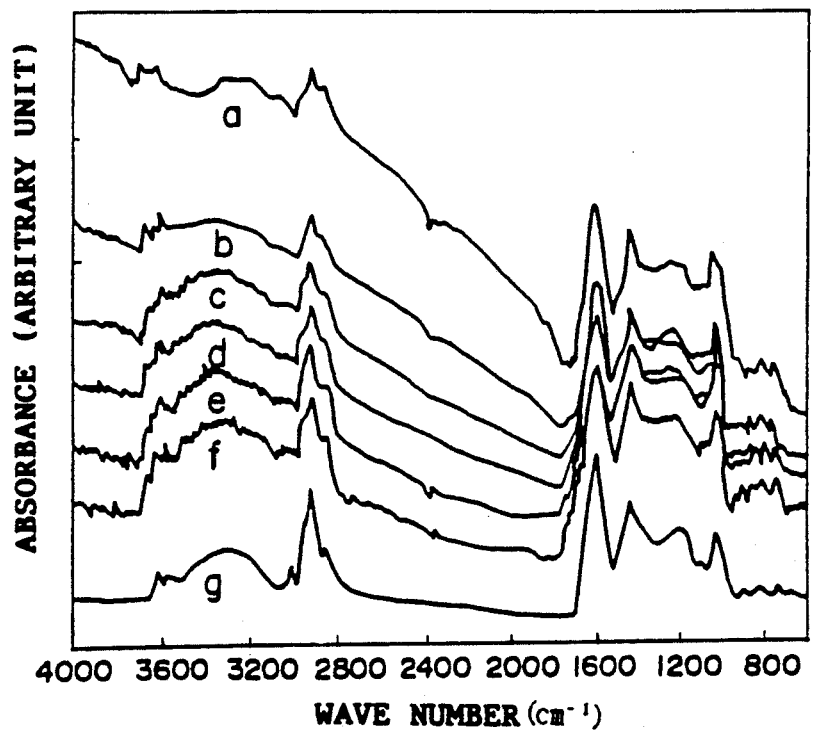
FIGS. 16 and 17 are graphs showing absorption spectra of samples measured using various accessories.

Infrared spectra were measured as shown in FIG. 10, and shown in FIG. 16.

Figure 15:
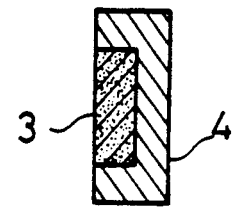
FIG. 15 is a sectional view of a pelletized sample and an infrared rays-scattering filter attached thereto.

The sample 3 was a coal powder, and it was pelletized with KBr. The filter 4 was made of a mixture of CsI fine powder (under 125 μm) and KBr fine powder (under 125 μm) mixed in various ratios, and molded by pressing under vacuum into the shape shown in FIG. 15. In FIG. 16, a indicates the conventional case, and the spectra a were measured without a reflecting mirror or filter. The spectra b through f were measured using the filter but not using a reflecting mirror, and the mixing ratio was 20 wt. % in the case of the spectra b, 30 wt. % in the case of the spectra c, 40 wt. % in the case of the spectra d, 50 wt. % in the case of the spectra e, and 60 wt. % in the case of the spectra f. The spectra g were measured using the filter containing 60 wt. % of CsI and a reflecting mirror.

Example 6

Figure 17:
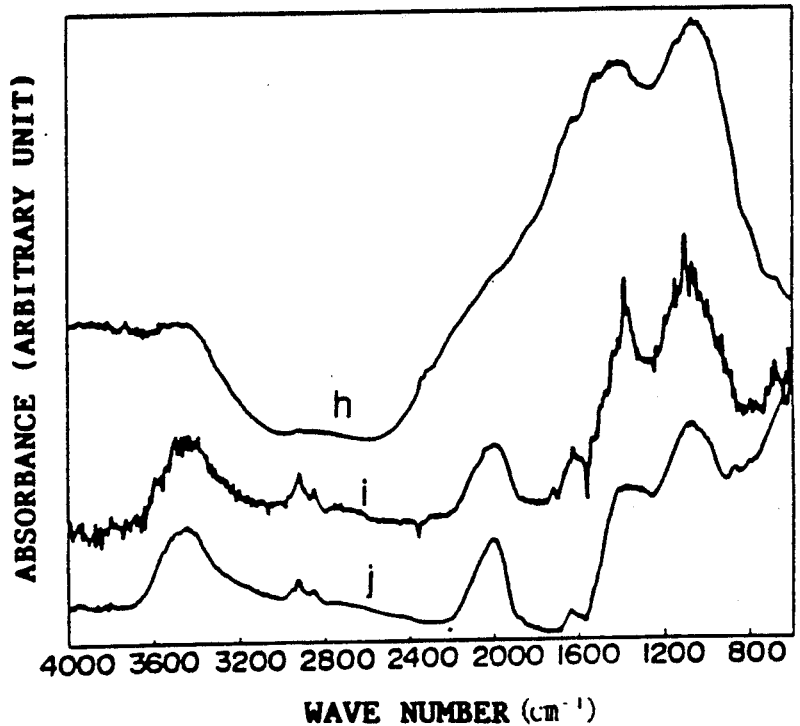

Infrared spectra obtained in another example are shown in FIG. 17.

The sample used was amorphous silicon powder, and it was pelletized by using KBr powder. In the figure, h indicates the conventional case, and the spectra i were measured using the filter made of a mixture of 60 wt. % of CsI fine powder (under 125 μm) and 40 wt. % of KBr fine powder (under 125 μm) and molded by pressing under vacuum into a disc. The spectra j were measured using the above filter and an ellipsoid mirror in the embodiment shown in FIG. 13. As shown in FIG. 17, a novel absorption peak appeared around 2000 cm$^{-1}$ in the spectra i which did not exist in the spectra h of the conventional case. Though components of the spectra i were great because of insufficient sensitivity, in the case of the spectra j, the vibration disappeared, and the peak height could be measured accurately.

We claim:

1. A dilution material for a sample whose infrared spectra is measured consisting essentially of two or more kinds of particles of inorganic materials having a particle size of less than 100 μm capable of transmitting infrared rays, of which the surface reflection loss is less than one third, and at least one of which the refractive index is different from another one by more than 0.1.

2. The dilution material of claim 1 essentially consisting of 5 to 95 wt. % of a first material and 95 to 5 wt. % of a second material.

3. The dilution material of claim 2 wherein the first material is cesium iodide having a mean particle size of less than 20 μm and the second material is potassium bromide having a means particle size of less than 20 μm.

4. An accessory for measuring infrared spectra comprising a prism or a reflecting mirror having an incident portion for infrared rays which is disposed surrounding a pelletized sample and an infrared rays-scattering filter being in contact with or close to the back of the pelletized sample, and which gathers scattered infrared rays and reflected infrared rays emitted from the pelletized sample through said filter.

5. The accessory of claim 4 wherein the infrared rays-scattering scattering filter is made of two or more kinds of the inorganic materials capable of transmitting infrared rays, of which the surface reflection loss is less then one third, and at least one of which the refractive index is different from another one by more than 0.1.

6. The accessory of claim 4 or claim 5 wherein the sample is pelletized by using a dilution material comprising two or more kinds of the inorganic materials capable of transmitting infrared rays, of which the surface reflection loss is less than one third, and at least one of which the refractive index is different from another one by more than 0.1.

7. A method of measuring infrared spectra which comprises disposing an infrared rays-scattering filter made of two or more kinds of the inorganic materials capable of transmitting infrared rays, of which the surface reflection loss is less than one third, and at least one of which the refractive index is different from another one by more than 0.1 behind a pelletized sample which is uniformly dispersed in a dilution material comprising two or more kinds of the inorganic materials capable of transmitting infrared rays, of which the surface reflection loss is less than one third, and at least one of which the refractive index is different from another one by more than 0.1, and measuring the infrared spectra.

8. The method of claim 7 wherein both of said comprising two or more kinds of the inorganic materials are essentially consisting of 5 to 95 wt. % of a first material and 95 to 5 wt. % of a second material, respectively.

9. A method of preparing two or more kinds of particles of inorganic materials having a particle size of less than 100 μm capable of transmitting infrared rays, of which the surface reflection loss is less than one third, and at least one of which the refractive index is different from another one by more than 0.1 which comprises depositing said two or more kinds of particles of inorganic materials having a particle size of less than 100 μm from an aqueous solution containing the two or more kinds of particles of inorganic materials having a particle size of less than 100 μm, and drying the deposited particles separated or not separated from the mother liquid.

* * * * *